Dec. 6, 1960 W. M. DALTON Plant Pat. 1,994
APPLE TREE
Filed Feb. 2, 1960
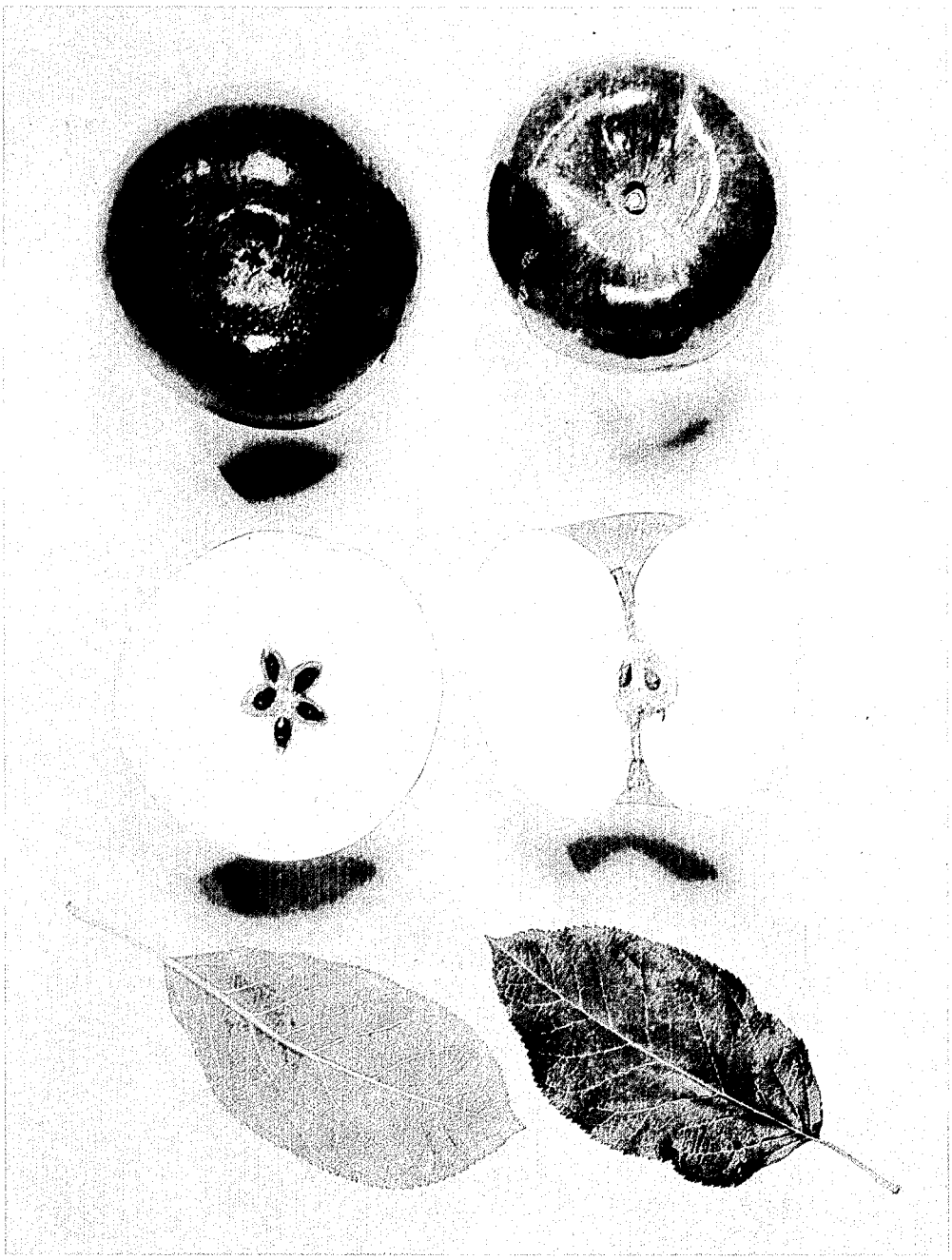
INVENTOR
Will Mills Dalton, Deceased
By: William Edward Dalton,
Administrator, C.T.A.
BY Robb & Robb ATTORNEYS United States Patent Office Plant Pat. 1,994
Patented Dec. 6, 1960

1,994

APPLE TREE

Will Mills Dalton, deceased, late of Hendersonville, N.C., by William Edward Dalton, administrator, c.t.a., Rt. 2, Hendersonville, N.C., assignor, by mesne assignments, to said William Edward Dalton Filed Feb. 2, 1960, Ser. No. 6,332

1 Claim. (Cl. 47—62)

The present invention relates to a new and distinct variety of apple tree which was originated by the late Will Mills Dalton, deceased, by crossing an unnamed and unpatented seedling of unknown parentage with the varieties "Red Delicious" (unpatented) and "King David" (unpatented), respectively.

While growing a number of different standard apple varieties on his cultivated orchard property near Hendersonville, North Carolina, said Will Mills Dalton, deceased, found an unusual seedling in this orchard which differed greatly from any other varieties being grown therein, as evidenced by the fact that the new seedling bore striped fruit of pale color, but of unusually large size—the size being approximately twice that of the fruit of the other adjacent standard varieties. The fruit of the new seedling was found to have a distinctive good flavor and superior keeping qualities, but its color was not considered sufficiently attractive to make it worthy of commercial use. He thereupon understook to improve the fruit of the original seedling by crossing it with two other varieties, as indicated above, and this resulted in the achievement of a new variety having improved fruit of good dark red color, entirely different from the fruit of the original seedling, combined with other desirable characteristics which represent a unique combination definitely differentiating the new variety from its parents, as well as from all other varieties of which he was aware. The outstanding features of this new combination are briefly described as follows:

(1) A semi-dwarf and open habit of tree growth;

(2) A habit of branch scaffolding at intervals of from 1½ to 3 feet, with consequent need of little or no pruning;

(3) A late-blooming habit—even later than "Rome Beauty" (unpatented), with consequent minimization of the likelihood of being subject to damage by frost;

(4) Extra-large size of the fruit—averaging approximately 4 inches in diameter;

(5) A ripening season approximating that of "Rome Beauty";

(6) A sub-acid fruit flavor;

(7) A dark red fruit color somewhat resembling that of "Double Red Stayman" (unpatented); and (8) Good scab resistance of both the foliage and fruit as compared with other varieties grown in the same orchard under the same cultural conditions, near Hendersonville, North Carolina, and in which all other varieties were heavily infested with scab.

Asexual reproduction of the new variety, as performed by grafting, at Hendersonville, North Carolina, shows that the foregoing characteristics and distinctions come true to form and are established and transmitted through succeeding propagations.

The accompanying drawing shows typical specimens of the foliage and fruit of the new variety as depicted in color as nearly true as it is reasonably possible to make the same in a color illustration of this character, certain of said specimens depicting both exterior and cross-sectional views of the fruit, as well as both the upper and lower surfaces of specimen leaves.

The following is a detailed description of the new variety, with color terminology in accordance with Maerz and Paul Dictionary of Color, except where general color terms of ordinary dictionary significance are obvious, as based upon observations made from specimens grown at Hendersonville, North Carolina:

Parentage: An unnamed seedling of unknown parentage × "Red Delicious" × "King David."

Dates of first and last pickings: About September 20 and about October 5, respectively; usually ripens with "Rome Beauty."

Tree: Medium size; medium vigor; spreading; low; open-topped; hardy; very productive; regular bearer; slow-growing.

*Truck.*—Medium stockiness; smooth.

*Branches.*—Medium thickness; smooth; little-branched. Color: old wood—Greenish Brown, Plate 16–9E; new wood—Reddish Brown, Plate 8–L2.

*Lenticels.*—Few; large.

*Leaves.*—Size—medium. Length—about 4 inches. Width—about 3 inches. Shape—oval; abruptly pointed; medium thickness; smooth. Color: upper side—Green, Plate 21–7E; under side—Fern Green, Plate 21–5F. Margin—crenate; coarsely serrate. Petiole—long (about 1⅛ inches); thick.

Flowers: Late, as compared with other varieties.

*Date of first and full bloom.*—About April 25 and May 4, respectively.

*Size.*—Small.

*Color.*—Pink, Plate 50–E4.

Fruit:

*Maturity when described.*—Eating-ripe (about November 19).

*Size.*—Uniform. axial diameter—about 3¼ inches. Transverse diameter—about 4 inches.

*Form.*—Uniform; symmetrical; regular; compressed laterally; truncate at base.

*Cavity.*—Symmetrical; flaring toward apex; evenly furrowed; pubescent toward apex. Depth—from about ½ inch to about ⅝ inch. Breadth—from about 1¼ inches to about 1½ inches.

*Markings.*—Slightly streaked toward apex.

*Basin.*—Symmetrical; rounded; flaring; wide base; evenly furrowed; glabrous.

*Stem.*—Clubbed; tout; pubescent; bracts wanting. Length—from about ¼ inch to about ⅜ inch.

*Calyx.*—Open. Segments—persistent; broadly lanceolate; about 1/16 inch long; separated; approximate at base; prostrate; reflexed at apex. Outer surface—pubescent. Inner surface—glabrous.

*Eye.*—Medium size; partially closed.

*Skin.*—Medium thickness; tough; smooth; glossy; waxed. Dots—conspicuous; few; small; even; oblong; color—brown; distribution—more toward base. Ground color—Greenish Yellow, Plate 10–H1. Color markings—splashed; Garnet Red and Wild Strawberry, Plate 6–K6.

*Bloom.*—Scant.

*Scarfskin.*—Gray-white. Distribution—light distribution at cavity.

*General color effect.*—Dark red.

*Flesh.*—Rather juicy. Color—satiny white, with yellowish tint. Texture—firm; crisp. Flavor—subacid; rich. Aroma—wanting. Quality—good.

*Core.*—Median; distant. Bundle area—medium size; broadly ovate; symmetrical; acute at base. Halves of core—equal. Bundles: color—yellowish. Alternate bundles—approximate to calyx tube; reaches tube above stamens. Core lines—meeting; distinct in cross section. Carpellary area—distinct; small. Calyx tube—pubescent toward apex; funnel form. Funnel stem—long. Depth of tube to shoulder—about ¾ inch; entire depth—about 1¼ inches.

*Styles.*—Present; united toward base; pubescent at point of branching.

*Stamens.*—In one distinct whorl; basal.

*Seed cells.*—Axile; open. Cell walls—approximate; thin; tough; length—about ⅜ inch; breadth—about ⅜ inch; longitudinal section—broadly ovate; mucronate at apex. Surface—smooth. Cross section—broad.

Seeds:

*Number.*—10 perfect; none imperfect; no more than 2 per cell.

*Length.*—About ⅜ inch.

*Breadth.*—From about 9/16 inch to about ¼ inch.

*Form.*—Acuminate.

*Color.*—Brown-chocolate, Plate 8–H10.

Use: Market; local; dessert; culinary.

Keeping quality: Good (about 120 days in ordinary common storage).

Disease resistance: Good resistance to scab, as determined by comparison with other varieties grown under the same cultural conditions at Hendersonville, North Carolina; neither fruit nor leaves have shown any evidence of scab even when prevalent in other varieties growing in same orchard.

General observations: The tree of the new variety compares more closely with that of the variety "Wolf River" (unpatented). It spreads out, but is not as thick or dense as "Wolf River" and it grows slower and never gets as large. At maturity, the tree is about ⅔ as large as the varieties "Stayman" (unpatented) or "Delicious" (unpatented). The limbs require little or no pruning because of their habit of scaffolding at relatively close intervals. The blooms of the new variety commence about 10 days later than "Delicious," or from about 5 to 7 days later than "Rome Beauty," and they are apparently self-pollinating because all other varieties have dropped their blooms at that time. The fruit resembles "Double Red Stayman" more in appearance and color, but it grows larger than most varieties, and ripens with "Rome Beauty."

He claims:

A new and distinct variety of apple tree, substantially as herein shown and described, characterized particularly as to novelty by the unique combination of a semi-dwarf and open habit of tree growth, a habit of branch scaffolding at relatively close intervals with consequent need of little of no pruning, a relatively late blooming habit, extra-large size of the fruit, a ripening season approximating that of "Rome Beauty" (unpatented), a subacid fruit flavor, dark red fruit color somewhat resembling that of "Double Red Stayman" (unpatented), and good scab resistance of both the fruit and foliage.

No references cited.